United States Patent

Zhu et al.

[11] Patent Number: 6,061,594
[45] Date of Patent: May 9, 2000

[54] ALGORITHM FOR AUTOMATICALLY CHECKING THE PACING SAFETY MARGIN IN CARDIAC PACING SYSTEMS

[75] Inventors: Qingsheng Zhu, Little Canada; Douglas J. Lang, Arden Hills, both of Minn.

[73] Assignee: Cardiac Pacemakers, Inc., St. Paul, Minn.

[21] Appl. No.: 09/124,796

[22] Filed: Jul. 29, 1998

[51] Int. Cl.[7] .................................................. A61N 1/37
[52] U.S. Cl. .............................................................. 607/28
[58] Field of Search .................................... 607/28, 27, 9

[56] References Cited

U.S. PATENT DOCUMENTS

| | | |
|---|---|---|
| 4,233,985 | 11/1980 | Hartlaub et al. . |
| 4,253,466 | 3/1981 | Hartlaub et al. . |
| 4,273,132 | 6/1981 | Hartlaub et al. . |
| 4,273,133 | 6/1981 | Hartlaub et al. . |
| 4,337,776 | 7/1982 | Daly et al. ................................ 607/28 |
| 4,401,120 | 8/1983 | Hartlaub et al. . |
| 4,895,152 | 1/1990 | Callaghan et al. ........................ 607/28 |
| 5,320,643 | 6/1994 | Roline et al. ............................. 607/28 |
| 5,350,410 | 9/1994 | Kleks et al. .............................. 607/28 |
| 5,391,192 | 2/1995 | Lu et al. ................................... 607/28 |
| 5,855,594 | 1/1999 | Olive et al. ............................... 607/28 |

Primary Examiner—Kennedy J. Schaetzle
Attorney, Agent, or Firm—Nikolai, Mersereau & Dietz, P.A.

[57] ABSTRACT

A method for automatically maintaining a desired safety margin associated with a current pacing output of the cardiac pacer to thereby minimize the need for backup pacing and maximize the efficiency of the cardiac pacer circuitry. The method may be implemented in a cardiac pacer to reduce power consumption while assuring therapeutic efficacy. In use, after a preselected lapse of time the pacing output is altered to determine whether the current pacing output should be increased, remain the same, or reduced.

37 Claims, 3 Drawing Sheets

ALGORITHM FOR AUTOMATICALLY CHECKING THE PACING SAFETY MARGIN IN CARDIAC PACING SYSTEMS

BACKGROUND OF THE INVENTION

I. Field of the Invention

The present invention relates generally to cardiac rhythm management devices capable of automatically adjusting an output of the cardiac rhythm management device. More particularly, the present invention relates to a device and method for automatically monitoring and adjusting the pacing output in a cardiac pacing system so as to maintain a desired pacing output safety margin and minimize power consumption while assuring therapeutic efficacy. The device and method of the present invention does not require an actual measurement or determination of the pacing threshold value in order to maintain the desired pacing output safety margin.

II. Discussion of the Prior Art

Over the years cardiac rhythm management devices have evolved such that capture verification and pacing output thresholds may now be determined automatically. For the most part, prior art implantable cardiac rhythm management devices, including bradycardia and tachycardia pacemakers, include both a sensing threshold and a pacing threshold. The success of a cardiac pacemaker in depolarizing or "capturing" the heart hinges on whether the energy of the pacing stimulus as delivered to the myocardium exceeds the hearts threshold requirements. This threshold requirement, referred to as the capture threshold or pacing output threshold, represents the amount of electrical energy required to initiate heart cell depolarization. If the energy of the pacing stimulus does not exceed the capture threshold, then depolarization will not result. If, on the other hand, the energy of the pacing stimulus exceeds the capture threshold, then depolarization results.

The sensing threshold is utilized during capture verification to determine whether a paced stimulus evokes a response having a value greater than the defined sensing threshold. The sensing threshold is necessary to avoid malsensing due to patient activity, body position, noise, or other factors. When verifying capture, the rhythm management device may have sense amplifier circuits for amplifying and filtering electrogram signals picked up by electrodes placed in or on the heart and which are coupled by suitable leads to the implantable cardiac rhythm management device. Typically, the signals emanating from the sense amplifier are applied to one input of a comparator circuit whose other input is connected to a source of reference potential. Only when an electrogram signal from the sense amplifier exceeds the reference potential threshold will it be treated as a capture or a sensed beat. The source reference potential may be referred to as a sensing threshold.

In order to maximize use of the limited power supply, it is desirable to set the lowest output energy that reliably results in capture of an electrical stimulus generated by the pulse generator, causing depolarization of the corresponding cardiac muscle. Although it is desirable to make the most efficient use of the cardiac rhythm management device's power supply, the pacing output is typically set at an energy output above the pacing threshold in order to compensate for changes in output demand. The changes in output demand may result from patient activity, body position, drugs being used, etc. To ensure the reliability of pacing, one common practice of setting the pacing output level is to determine the minimum output energy that induces a cardiac depolarization (the actual pacing output threshold), and then set the pacemaker's output at this minimum setting plus a wide error margin. The error margin is usually set at double or triple the determined effective minimum output energy. This error margin is meant to account for the changes in energy requirements that may occur between adjustments of the pacing output. The error margin may result in an unnecessary drain of the limited power supply. Also, during the determination of the actual pacing output threshold, one or more back-up paces may typically be required, thereby further draining the limited power supply.

The ability to minimize the required output energy while maintaining capture is extremely desirable in that delivering stimulation pulses having energy far in excess of the patient's capture threshold is wasteful of the pacemaker's limited power supply. Further, delivery of stimulation pulses far in excess of the patient's capture threshold may require additional complex circuitry. Further, the actual determination of the capture threshold is an added strain on the power supply. Therefore, a need exists for a rhythm management device that automatically adjusts the pacing output such that the pacing output is maintained at a level approximating the energy output of the power supply, while maintaining a desired pacing output safety margin. The present invention meets these and other needs.

SUMMARY OF THE INVENTION

The purpose of the present invention is to provide an improved device and method of pacing the heart of a patient. The improved pacing device and method automatically seeks to minimize power consumption while assuring therapeutic efficacy. The device includes a control means for adjusting the pacing output. From time to time the output demand may require that the pacing output be increased above a predetermined set point. Once the pacing output is increased above the predetermined set point, the control means determines whether the pacing output level may be adjusted toward the desired set point, while maintaining a desired pacing output safety margin and without requiring an actual threshold measurement or determination.

The device and pacing method of the present invention utilizes an improved output circuit for use in the cardiac pacemaker that attenuates polarization voltages or "afterpotential" which develop at the heart tissue/electrode interface following the delivery of a pacing stimulus to the heart tissue. Use of the improved output circuit allows an evoked response of the heart to be accurately detected to determine whether the pacing stimulus resulted in heart capture or contraction. The improved output circuit is further disclosed and described in greater detail in co-pending application Ser. No. 08/977,272, filed Nov. 24, 1997, now U.S. Pat. No. 5,843,136 and Ser. No. 09/088,864 filed Jun. 2, 1998 and assigned to the same assignee as the present application, the entire disclosures of which are incorporated herein by reference for any purpose.

Generally, changes in the pacing output threshold or capture threshold may be detected by monitoring the efficacy of stimulating pulses at a given energy level. If capture does not occur at a particular stimulation energy level which previously was adequate to effect capture, then it can be surmised that the pacing output demand or capture threshold has increased and that the stimulation energy should be increased. On the other hand, if capture occurs consistently at a particular stimulation energy level over a relatively large number of successive stimulation cycles, then it is possible that the capture threshold has decreased such that the stimulation energy is being delivered at a level higher than necessary to effect capture. This can be verified by decreasing the stimulation energy level and monitoring for loss of capture at the new energy level.

The improved pacing method may utilize a conventional cardiac rhythm management device of the type having means for sensing atrial and/or ventricular events, a programmable controller coupled to the sensing means, means for tracking beats of the heart, and means controlled by the controller for pacing the heart. The method in the preferred embodiment includes the steps of first pacing the heart of a patient at an initial pacing output. The pacing output preferably approximates the energy output of the power supply. This pacing output is identified as the preferred set point for the pacing output level. Without any limitation intended, in the preferred embodiment, the initial pacing output is 2.0 volts for 0.5 milliseconds. Of course, those skilled in the art will appreciate that the initial pacing output is patient dependent and may vary from patient to patient, however an initial pacing output of 1.0–3.5 volts may be adequate. Also, the duration of the pacing output may range between 0.2–1.0 milliseconds.

Once a preselected amount of time has lapsed, the pacing output is reduced by a first preset amount for a predetermined number of beats. The first preset amount may be set as a function of the pacing output. For example, the value associated with the first preset amount may be set equal to a varying percentage of the pacing output, wherein the varying percentage increases as the output decreases and the varying percentage decreases as the output increases (without any limitation intended, the preset amount may be set equal to 20% of the output for a pacing output of 5.0 volts and may be set equal to 50% of the output for a pacing output of 1.0 volts). Without any limitation intended, in the preferred embodiment the pacing output is reduced over at least four beats. Conventional means within the controller may be utilized to determine whether the reduced pacing output was captured by the heart of the patient. If the reduced pacing amount is not captured, a backup pulse is instituted and the pacing output level is increased by a preset amount in order to maintain the desired pacing safety margin. If there is capture at the first reduced pacing amount, then pacing continues at the preferred set point for the pacing output level.

If the pacing output level has been increased above the preferred set point, after a predetermined amount of time has lapsed, the pacing output is reduced by the first preset amount and a determination is made whether the first reduced pacing output was captured by the heart of the patient. The first preset amount may be set as a function of the pacing output. If the first reduced pacing output is captured, the pacing output is reduced to a second preset amount for a predetermined number of beats. The second preset amount may be set as a function of the pacing output. The means within the controller then determines whether the second reduced pacing output was captured by the heart of the patient. If the second reduced pacing output is captured, then pacing resumes at the first decreased pacing output, otherwise a backup pulse is instituted and pacing resumes at the initial pacing output. Pacing then continues for a predetermined lapse of time before the next automatic pacing output safety margin check is performed. Those skilled in the art will appreciate that the predetermined lapse of time may be variable. The automatic checking of the pacing output safety margin is bypassed if the initial pacing output is less than a predetermined amount.

OBJECTS

It is accordingly a principal object of the present invention to provide an improved method of pacing a patient's heart that automatically maintains the desired pacing output safety margin in a cardiac pacing system without requiring an actual threshold measurement or determination.

It is a further object of the present invention to provide an improved cardiac pacing method which minimizes the current drain on the power supply of the cardiac pacer to thereby prolong the life of the power supply.

Another object of the present invention is to provide an improved cardiac pacing method, wherein the pacing output level approximates the power supply voltage output.

These and other objects as well as these and other features of the present invention will become readily apparent to those skilled in the art from a review of the following detailed description of the preferred embodiment especially when considered in conjunction with the claims and accompanying drawings in which like numerals in the several views refer to corresponding parts.

DETAILED DESCRIPTION OF THE PREFERRED EMBODIMENT

Figure 1:
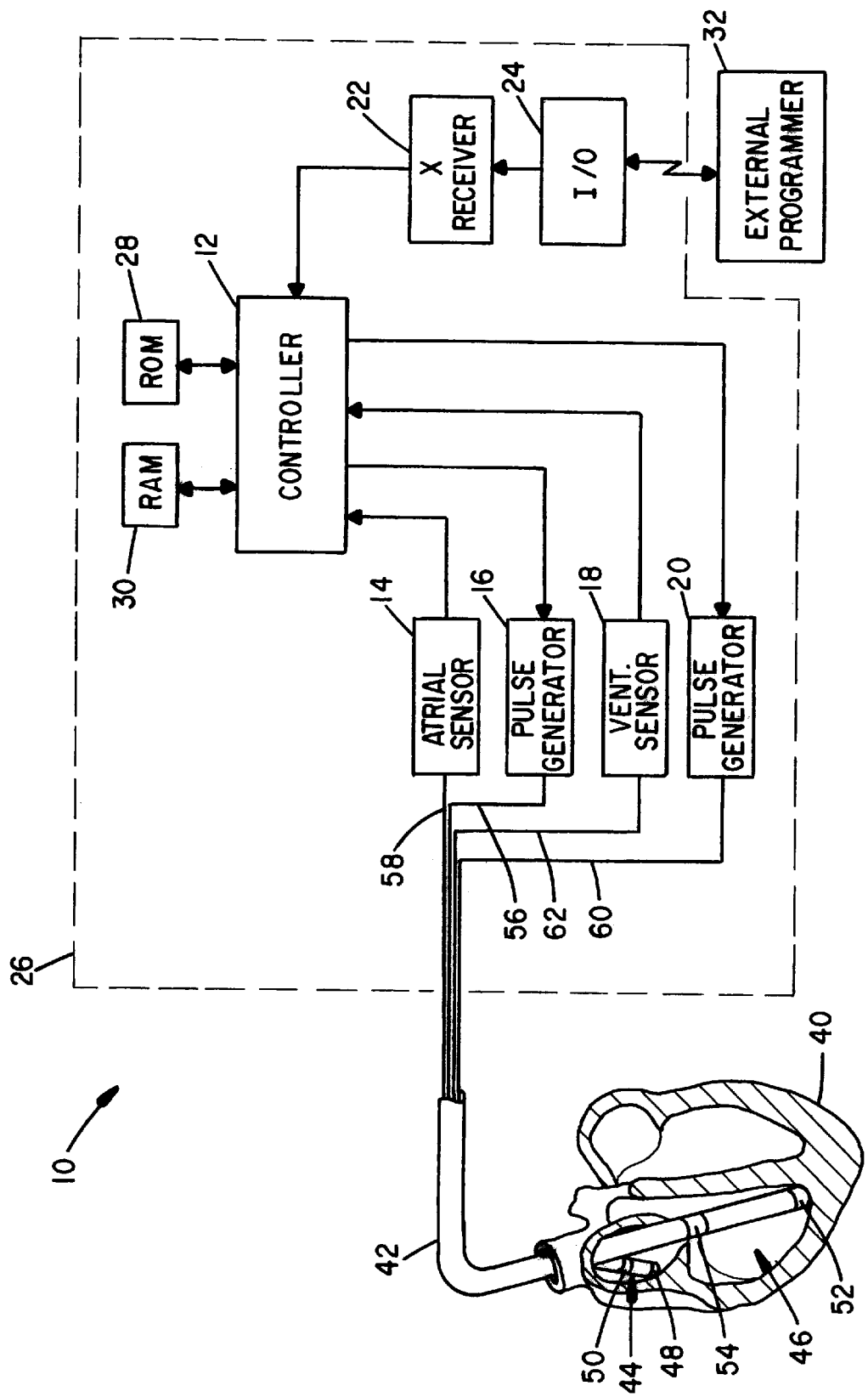
FIG. 1 is a block diagram depicting a cardiac pacer coupled to a lead positioned within a patient's heart.

The present invention may find application in a variety of implantable or external cardiac rhythm management devices, including but not limited to bradycardia pacemakers, antitachycardia pacemakers, and defibrillators, but for purposes of explanation, will be described in connection with an implantable rate adaptive cardiac pacemaker 10 as illustrated in FIG. 1. By way of illustration and not limitation, the cardiac pacemaker 10 is a dual chamber (DDD) pacer having a controller 12 operatively coupled to an atrial sense amplifier 14, an atrial pulse generator 16, a ventricular sense amplifier 18, a ventricular pulse generator 20, a transceiver 22, and an input/output module 24, all of which are disposed within a hermetically sealed housing designated by a dotted line at 26. The cardiac pacemaker 10 also includes read-only memory (ROM) 28 and random access memory (RAM) 30 communicatively coupled to the controller 12. The transceiver 22 is cooperatively operable with input/output module 24 for transmitting and receiving information to and from an external programmer 32.

The cardiac pacemaker 10 is operatively coupled to a patient's heart 40 via a main pacing lead 42 which splits into an atrial lead 44 and a ventricular lead 46. Those skilled in the art will appreciate that separate atrial and ventricular leads may be utilized, however a split lead is shown and described for clarity and ease of discussion. Bipolar pacing is provided, by way of example, wherein the atrial lead 44 has a tip electrode 48 and a ring electrode 50, and the ventricular lead 46 has a tip electrode 52 and a ring electrode 54. The atrial pulse generator 16 is electrically coupled to the tip electrode 48 of the atrial lead 44 via a conductor 56 for delivering stimulating pulses to the atrium under the direction of the microprocessor controller 12. The atrial sense amplifier 14 is electrically coupled to the ring electrode 50 of the atrial lead 44 via a conductor 58 for sensing the occurrence of P-wave activity relating to atrial events and forwarding this atrial information to the controller 12.

The ventricular pulse generator 20 is similarly electrically coupled to the tip electrode 52 of the ventricular lead 46 via a conductor 60 for delivering stimulus pulses to the ventricle under the direction of the controller 12. The ventricular sense amplifier 18 is electrically coupled to the ring electrode 54 of the ventricular lead 46 via a conductor 62 for sensing the R-wave activity relating to ventricular depolarization and forwarding this ventricular information to the controller 12. Of course a single pulse generator may be utilized to deliver pacing stimulus to the atrium and ventricles under the direction of a controller having the necessary components known to those skilled in the art.

Figure 2:
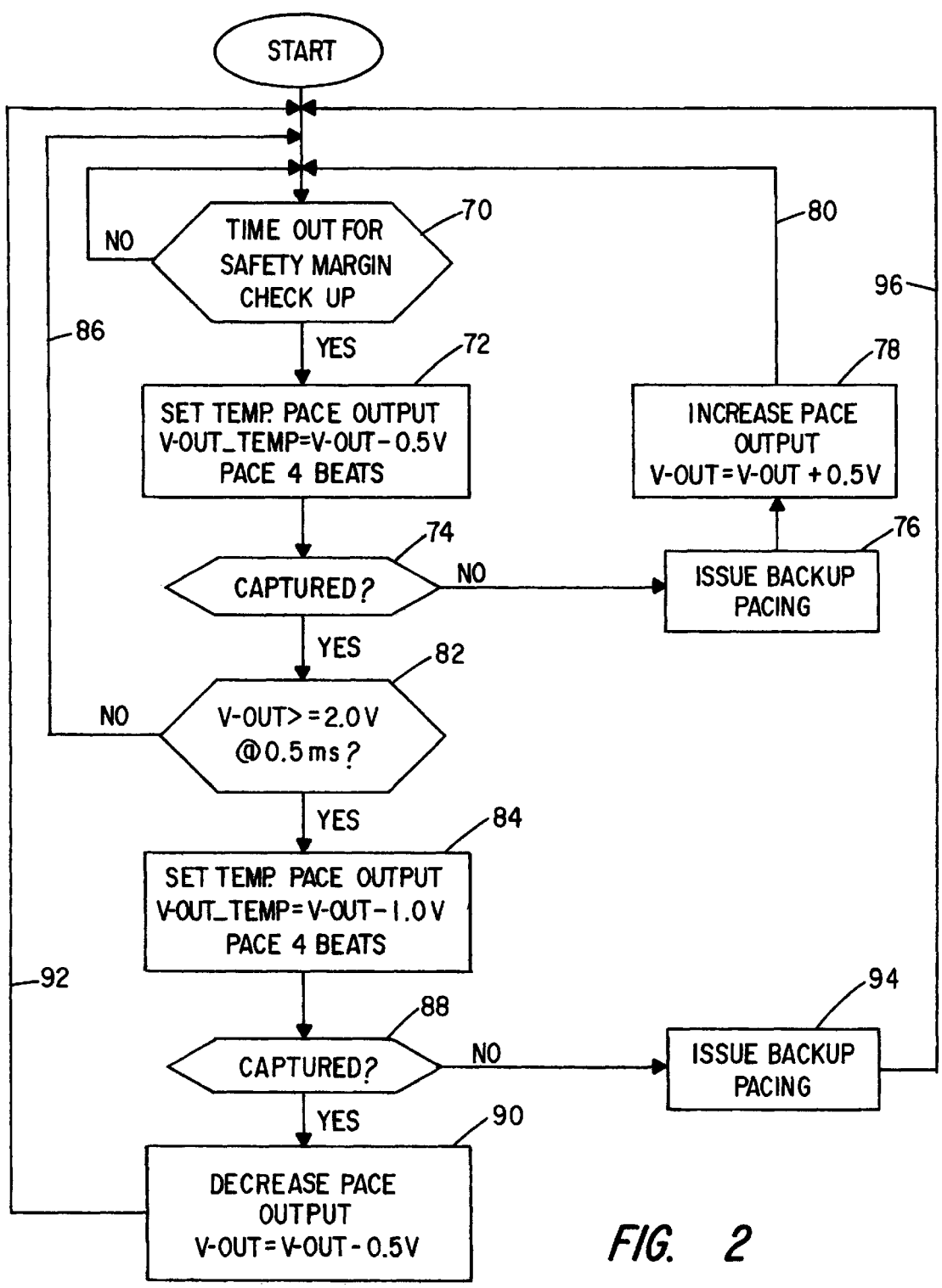
FIG. 2 is a flow diagram of the algorithm used to run the cardiac pacer's automatic checking the pacing safety margin in accordance with the present invention.

Although the method of the present invention may utilize the cardiac pacer shown in FIG. 1, it is to be understood that other known cardiac rhythm management devices may utilize the method of the present invention and the description of particular components of the cardiac rhythm management device should not be construed as limiting. Referring now to FIG. 2, one preferred method of the present invention is illustrated in flow chart form. The heart of the patient is initially paced at a predetermined initial or normal pacing output. The cardiac pacer 10 includes a timing means of suitable known construction that initiates the pacing output safety margin check after a predetermined amount of time has lapsed (see decision block 70). Once the predetermined amount of time has lapsed, the pacing output is reduced by a first preset amount for a predetermined number of beats. This is accomplished by setting a temporary pacing output equal to the initial pacing output minus a preset amount (see block 72). Without limitation, although specific pacing outputs and durations have been included, these amounts should not be construed as limiting the scope of the present invention. For example, although the preset amount is identified in block 72 as being 0.5 volts, those skilled in the art will appreciate that preset amount may vary with a range between 0.2 volts to 1.0 volts, with 0.5 volts being preferred and further may be set as a function of the pacing output as described above in greater detail. The pacer utilizes this temporary pacing output over a predetermined number of beats and checks to see if the pacing output results in capture (see decision block 74). If capture does not result from the first reduced pacing output, then the heart is paced with backup pacing (see block 76) and the normal pacing output is increased by a predetermined amount (see block 78). Although the preset amount is identified in block 78 as being 0.5 volts, those skilled in the art will appreciate that preset amount may vary with a range between 0.2 volts to 1.0 volts being preferred, and further may be set as a function of the pacing output as described above in greater detail. The normal pacing then continues until the next time the timing means times out (see loop 80).

If the first temporary pacing output is captured at block 74 and the normal pacing output exceeds a predetermined amount (see decision block 82), then the temporary pacing output is reduced by a second preset amount for a predetermined number of beats (see block 84). Although the preset amount is identified in block 84 as being 1 volt, those skilled in the art will appreciate that preset amount may vary with a range between 0.4 volts to 2.0 volts and further may be set as a function of the pacing output. In one embodiment of the present invention, if the normal pacing output does not exceed a predetermined amount at decision block 82 then the timing means is reset and pacing continues at the normal pacing output until the timing means times out (see loop 86). If the second reduced pacing output results in capture (see decision block 88) then the normal or initial pacing output is reduced to equal the first reduced pacing output (see block 90), the timing means is reset, and pacing continues at the reduced pacing output until the timing means times out (see loop 92). If capture does not occur at decision block 88, the backup pacing is instituted (see block 94), the timing means is reset, and pacing continues at the normal or initial pacing output until the timing means times out (see loop 96). In the preferred embodiment, the initial or normal pacing output voltage is approximately equal to the voltage output of the power supply. In this manner, a desired pacing safety margin is maintained without maintaining an excessively high pacing safety margin.

Figure 3:
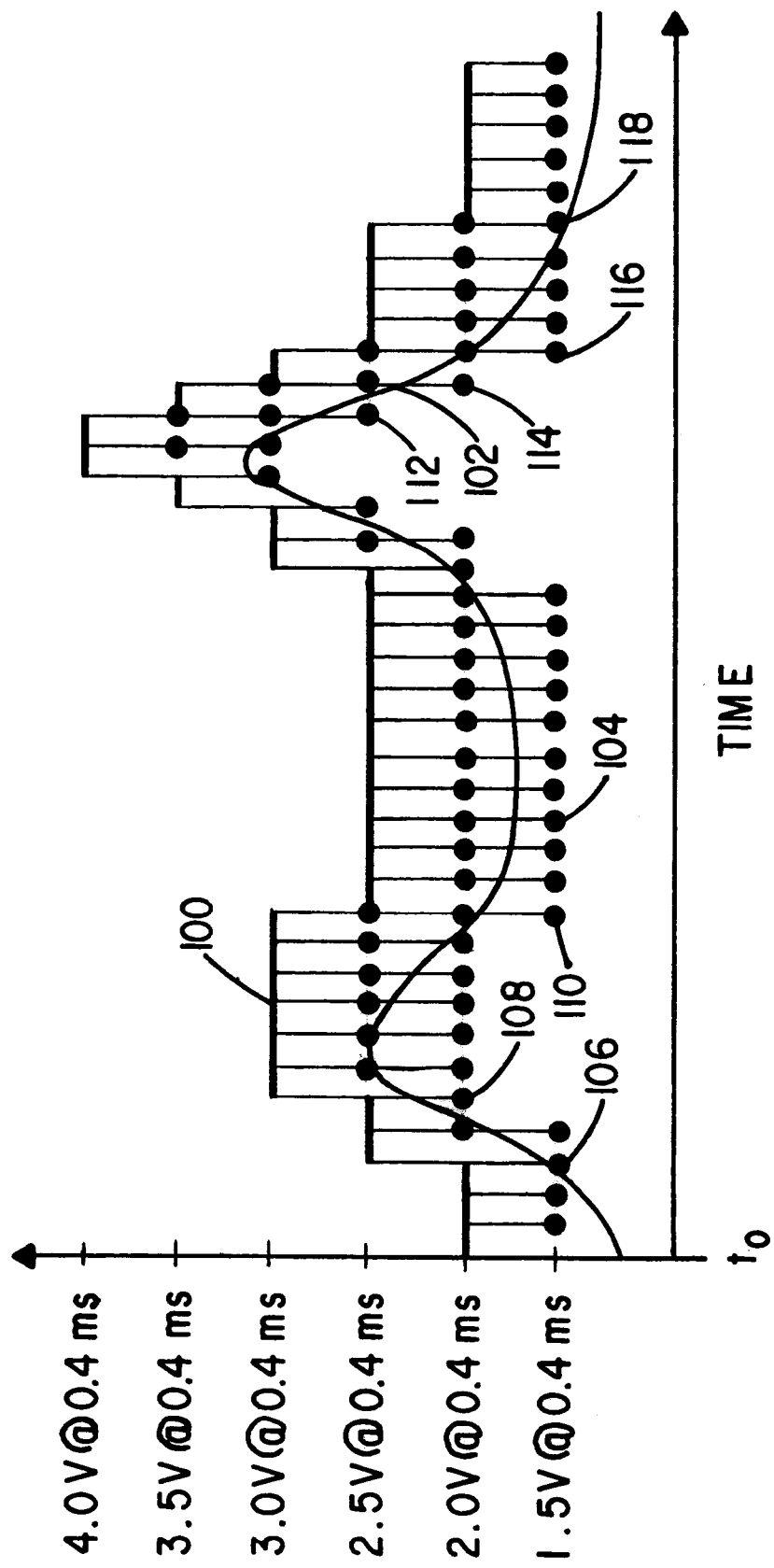
FIG. 3 is a graph illustrating the maintenance of the desired pacing safety margin as the pacing threshold varies over time.

Turning now to FIG. 3, the maintenance of the desired pacing safety margin is shown as the estimated pacing threshold varies over time. The pacing output, represented by line 100, remains at the desired pacing output level, unless the output demands require an increase in the pacing output. For ease of discussion and understanding, an estimated pacing threshold is shown as line 102. Periodically, the pacing output is lowered a predetermined amount and capture verification is undertaken, which is represented by solid circle 104. Beginning at to the pacing output level is set such that when the pacing output is reduced by a predetermined amount, the lowered pacing output is captured by the heart (the lowered pacing output is above the pacing threshold). As seen at point 106, when the pacing output is lowered, the lowered pacing output is below the pacing threshold and thus the lowered pacing output at point 106 is not captured. Thus, the pacing output is then increased a predetermined amount, thereby adjusting the pacing output safety margin.

The pacing output continues at the increased output (2.5 volts) until the periodic reduced pacing output does not result in capture, as at 108, at which point the pacing output level is again increased. When the pacing output is above the predetermined preferred pacing output, the pacing output will be reduced, if, during the periodic safety margin checks, capture is sensed for a twice reduced pacing output level as at 110, 112, 114, or 116. When the pacing output level reaches the preferred pacing output level, the pacing output is not reduced further. Those skilled in the art will appreciate that the preferred pacing output level may be greater or less than 2.0 volts and the frequency of the periodic check of the pacing safety margin may be varied from patient to patient and may occur as frequently as every few seconds, minutes, hours, or even days.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself

What is claimed is:

1. A method of pacing the heart of a patient, said method utilizing a cardiac rhythm management device of the type having sensing means for sensing atrial and ventricular events, a controller coupled to the sensing means, means for tracking beats of the heart, and means controlled by the controller for pacing the heart, the method comprising the steps of:

a) pacing the heart of a patient at a first pacing output level;

b) increasing a pacing output level of the cardiac rhythm management device above the first pacing output level when a pacing output demand increases;

c) after a preselected lapse of time, determining whether the pacing output level may be adjusted towards the first pacing output level without an actual determination of the pacing output threshold wherein a multiple step down pacing protocol is implemented; and d) lowering the pacing output level towards the first pacing output level if it is determined that the pacing output level may be lowered towards the first pacing output level.

2. The method as recited in claim 1, wherein steps c)–d) are omitted if the pacing output level is equal to the preset pacing output level.

3. The method as recited in claim 1, wherein the preset pacing output level is in the range between 1.0 volts to 3.5 volts.

4. The method as recited in claim 2, wherein the preset pacing output level is in the range between 1.0 volts to 3.5 volts.

5. The method as recited in claim 1, wherein the preselected lapse of time is variable.

6. A method of pacing the heart of a patient, said method utilizing a cardiac rhythm management device of the type having sensing means for sensing atrial and ventricular events, a controller coupled to the sensing means, means for tracking beats of the heart, and means controlled by the controller for pacing the heart, the method comprising the steps of:

a) pacing the heart of a patient at a pacing output sufficient to meet a pacing output demand of the patient's heart;

b) increasing the pacing output of the cardiac rhythm management device when a pacing output demand increases;

c) reducing after a preselected lapse of time the pacing output to a first reduced pacing output for a predetermined number of beats;

d) determining whether the first reduced pacing output was captured by the heart of the patient;

e) reducing the pacing output to a second reduced pacing output for a predetermined number of beats, if the first reduced pacing output is captured;

f) determining whether the second reduced pacing output was captured by the heart of the patient;

g) decreasing the pacing output to equal the first reduced pacing output, if the second reduced pacing output is captured.

7. The method as recited in claim 6, wherein the pacing output is in the range between 1.0 to 3.5 volts.

8. The method as recited in claim 6, wherein the first reduced pacing output is set as a function of a preselected pacing output.

9. The method as recited in claim 6, wherein the second reduced pacing output is set as a function of a preselected pacing output.

10. The method as recited in claim 6, wherein the predetermined number of beats is at least 4.

11. The method as recited in claim 10, wherein the first reduced pacing output is set as a function of a preselected pacing output.

12. The method as recited in claim 10, wherein the second reduced pacing output is set as a function of a preselected pacing output.

13. The method as recited in claim 6, wherein the preselected lapse of time is variable.

14. A method of pacing the heart of a patient, said method utilizing a cardiac rhythm management device of the type having sensing means for sensing atrial and ventricular events, a controller coupled to the sensing means, means for tracking beats of the heart, and means controlled by the controller for pacing the heart, the method comprising the steps of:

a) pacing the heart of a patient at an initial pacing output;

b) reducing after a preselected lapse of time the initial pacing output by a first preset amount for a predetermined number of beats;

c) determining whether the first reduced pacing output was captured by the heart of the patient;

d) pacing the heart with backup pacing if the first reduced pacing output is not captured and then pacing at the initial pacing output;

e) reducing the pacing output by a second preset amount for a predetermined number of beats, if the first reduced pacing output is captured;

f) determining whether the second reduced pacing output was captured by the heart of the patient;

g) pacing the heart with backup pacing if the second reduced pacing output is not captured and then pacing at the initial pacing output; and then h) decreasing the pacing output to equal the first reduced pacing output.

15. The method as recited in claim 14, wherein steps e)–h) are omitted if the initial pacing output is less than a predetermined amount.

16. The method as recited in claim 14, wherein the initial pacing output may range between about 1.0 to 3.5 volts.

17. The method as recited in claim 15, wherein the initial pacing output may range between about 1.0 to 3.5 volts.

18. The method as recited in claim 14, wherein the predetermined number of beats is at least 4.

19. The method as recited in claim 15, wherein the preselected lapse of time is variable.

20. The method as recited in claim 14, wherein the first preset amount is set as a function of a preselected pacing output.

21. The method as recited in claim 14, wherein the second preset amount is set as a function of a preselected pacing output.

22. A device for pacing the heart of a patient and automatically checking the pacing safety margin, said device comprising:

(a) pacing means for pacing the heart of a patient at a pacing output sufficient to meet a pacing output demand of the patient's heart, wherein the pacing output is increased when a pacing output demand increases;

(b) sensing means for sensing atrial and ventricular events; and (c) control means electrically coupled to the pacing means and sensing means, wherein the control means during an automatic pacing safety margin determination reduces the pacing output to a first reduced pacing output for a predetermined number of beats, determines whether the first reduced pacing output is captured by the heart of the patient, reduces the pacing output to a second reduced pacing output for a predetermined number of beats if the first reduced pacing output is captured, determines whether the second reduced pacing output is captured by the heart of the patient, and decreases the pacing output to equal the first reduced pacing output if the second reduced pacing output is captured.

23. The device as recited in claim 22, wherein the pacing output is in the range between 1.0 to 3.5 volts.

24. The device as recited in claim 22, wherein the first reduced pacing output is set as a function of the pacing output.

25. The device as recited in claim 22, wherein the second reduced pacing output is set as a function of the pacing output.

26. The device as recited in claim 22, wherein the predetermined number of beats is at least 4.

27. The device as recited in claim 26, wherein the first reduced pacing output is set as a function of the pacing output.

28. The device as recited in claim 26, wherein the second reduced pacing output is set as a function of the pacing output.

29. The device as recited in claim 22, wherein the preselected lapse of time is variable.

30. A device for pacing the heart of a patient and automatically checking the pacing safety margin, said device comprising:

(a) a pulse generator that generates stimulation pulses for delivery to a patient's heart at a pacing output sufficient to meet a pacing output demand of the patient's heart, wherein the pacing output is increased when a pacing output demand increases;

(b) sensing circuit for sensing atrial and ventricular events; and (c) a controller electrically coupled to the pulse generator and sensing circuit, wherein the controller during an automatic pacing safety margin determination reduces the pacing output to a first reduced pacing output for a predetermined number of beats, determines whether the first reduced pacing output is captured by the heart of the patient, reduces the pacing output to a second reduced pacing output for a predetermined number of beats if the first reduced pacing output is captured, determines whether the second reduced pacing output is captured by the heart of the patient, and decreases the pacing output to equal the first reduced pacing output if the second reduced pacing output is captured.

31. The device as recited in claim 30, wherein the pacing output is in the range between 1.0 to 3.5 volts.

32. The device as recited in claim 30, wherein the first reduced pacing output is set as a function of the pacing output.

33. The device as recited in claim 30, wherein the second reduced pacing output is set as a function of the pacing output.

34. The device as recited in claim 30, wherein the predetermined number of beats is at least 4.

35. The device as recited in claim 34, wherein the first reduced pacing output is set as a function of the pacing output.

36. The device as recited in claim 34, wherein the second reduced pacing output is set as a function of the pacing output.

37. The device as recited in claim 30, wherein the preselected lapse of time is variable.

* * * * *